(12) United States Patent
Kaplan et al.

(10) Patent No.: US 6,913,900 B2
(45) Date of Patent: Jul. 5, 2005

(54) PLASMA PREKALLIKREIN ACTIVATION AND KALLIKREIN PRODUCTION ASSAY

(75) Inventors: Allen P. Kaplan, Charleston, SC (US); Kusumam Joseph, Mt. Pleasant, SC (US)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 320 days.

(21) Appl. No.: 10/227,234

(22) Filed: Aug. 23, 2002

(65) Prior Publication Data

US 2003/0049713 A1 Mar. 13, 2003

Related U.S. Application Data

(60) Provisional application No. 60/315,800, filed on Aug. 29, 2001.

(51) Int. Cl.[7] .............................. C12Q 1/37; C12N 9/50; A61K 35/14
(52) U.S. Cl. ......................... 435/23; 435/219; 530/384
(58) Field of Search ................................ 435/219, 226; 424/185.1; 530/350, 384, 381

(56) References Cited

U.S. PATENT DOCUMENTS

| | | |
|---|---|---|
| 4,335,203 A | 6/1982 | Lasser |
| 4,598,043 A | 7/1986 | Svendsen |
| 4,882,272 A | 11/1989 | Scott et al. |
| 4,985,254 A | 1/1991 | Konishi |
| 4,985,354 A | 1/1991 | Toyomaki et al. |
| 5,013,558 A | 5/1991 | Konishi |
| 5,057,324 A | 10/1991 | Shibayama et al. |
| 5,560,935 A | 10/1996 | Konishi et al. |
| 5,599,683 A | 2/1997 | Nishikawa et al. |
| 5,648,228 A | 7/1997 | Nishikawa et al. |
| 6,117,648 A | 9/2000 | Shibayama et al. |

FOREIGN PATENT DOCUMENTS

| | | |
|---|---|---|
| EP | 0 341 209 A2 | 11/1989 |
| EP | 0 637 632 | 1/1991 |
| GB | 697351 | 9/1953 |
| JP | 53101515 | 9/1978 |
| JP | 57077697 | 5/1982 |
| JP | 58035117 | 3/1983 |
| JP | 63-185398 | 1/1991 |
| JP | 7051097 | 2/1995 |
| JP | 7051098 | 2/1995 |

OTHER PUBLICATIONS

Dreher D et al. 1995. Effects of oxidative stress and Ca2+ agonists on molecular chaperones in human umbilical vein endothelial cells. Electrophoresis. 16(7):1205–14.*

Kaplan, A., et al., "Assessment of Hageman Factor Activation in Human Plasma: Quantification of Activated Hageman Factor–C1 Inactivator Complexes by an Enzyme–Linked Differential Antibody Immunosorbent Assay," *Blood*, vol. 66, No. 3 (Sep.) 1985, pp. 636–641.

Gallimore, M.J., et al., "A Direct Chromogenic Peptide Substrate Assay for Hageman Factor (FXII)," *J. of Fibrinolysis*, 1(2), 1987, pp. 123–127.

Dumenco, L., et al., "Inhibition of the Activation of Hageman Factor (Factor XII) by Platelet Factor 4," *J. Lab. Clin. Med.*, 112(3), 1988, pp. 394–400.

Ghebrehiwet, B., "Identification of Functional Domans on GC1Q–R, a Cell Surface Protein That Binds to the Globular Heads of C1Q, Using Monoclonal Antibodies and Synthetic Peptides," *Hybridoma*, 15(5):333–342, May 1996.

Kusumam, J., "Identification of the Zinc Dependent Endothelial Cell Binding Protein for High Molecular Weight Kininogen and FXII," *Proc Natl Acad Sci USA*, 93:8552–8557, Aug. 1996.

Kaplan, A., "Binding of Activation of Kinin Forming Proteins on Vascular Endothelial Cells," *Immunopharmacology*, 36:201–207, 1997.

Herwald et al., "Isolation and Characterization of the Kininogen–binding Protein p33 from Endothelial Cells," *J. Biological Chem.*, vol. 271, No. 22, pp. 13040–13047, May 31, 1966.

Ghebrehiwet et al., "Isolation cDNA Cloning, and Overexpression of a 33–kD Cell Surface Glycoprotein that Binds to the Globular 'Heads' of C1q," *J. Exp. Medicine*, vol. 179, No. 6, pp. 1809–1821, Jun. 1994.

Motta Guacyara et al., "High molecular weight kininogen regulates prekallikrein assembly and activation and endothelial cells: A novel mechanism for contact activation", *BLOOD*, vol. 91, No. 2, Jan. 15, 1998, pp. 516–528, XP–002262835.

Joseph Kusuman et al., "Heat shock protein 90 catalyzes activation of the prekallikrein–kininogen complex in the absence of factor XII", Proceedings of the National Academy of Sciences of the United States, vol. 99, No. 2, Jan. 22, 2002, pp. 896–980, XP–002262836.

* cited by examiner

*Primary Examiner*—Sandra E. Saucier
*Assistant Examiner*—Lora E Barnhart
(74) *Attorney, Agent, or Firm*—Holland Law Firm, P.L.C.

(57) ABSTRACT

A activator for prekallikrein includes isolated, purified, or substantially purified heat shock protein 90, a phosphate ion, and mixtures thereof. The prekallikrein activator is part of an in vitro system for activating prekallikrein in the absence of FXIIa. The system includes the activator, high-molecular weight kininogen, and zinc ions. A method for activating prekallikrein to produce kallikrein in the absence of FXIIa includes mixing prekallikrein with the activator and a composition comprising high molecular weight kininogen and zinc ions. A method for evaluating the activity of a test drug for the production of kallikrein comprises activating prekallikrein and determining the kallikrein produced. The activity (promoting or inhibiting ability) of the tested drug against the production of kallikrein in the absence of FXIIa can be easily measured. The test drug may be an analgesic, anti-allergy, anti-inflammatory drug.

23 Claims, 4 Drawing Sheets

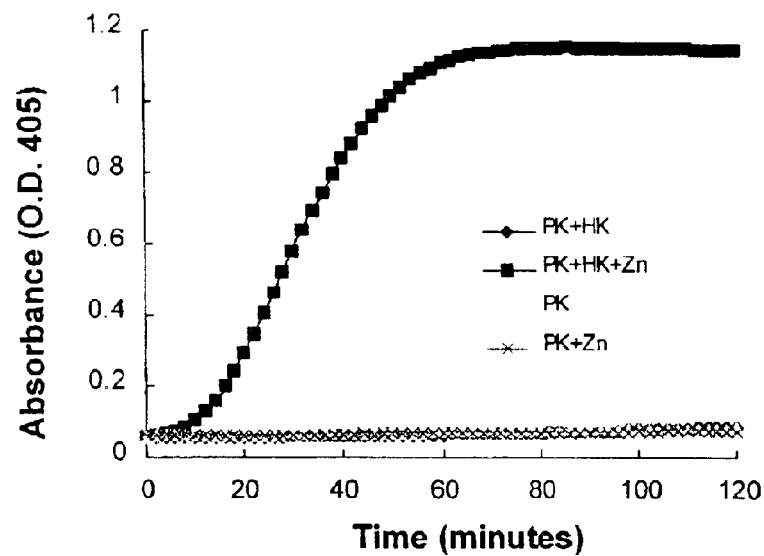
Figure 1  Prekallikrein activation on HUVEC.
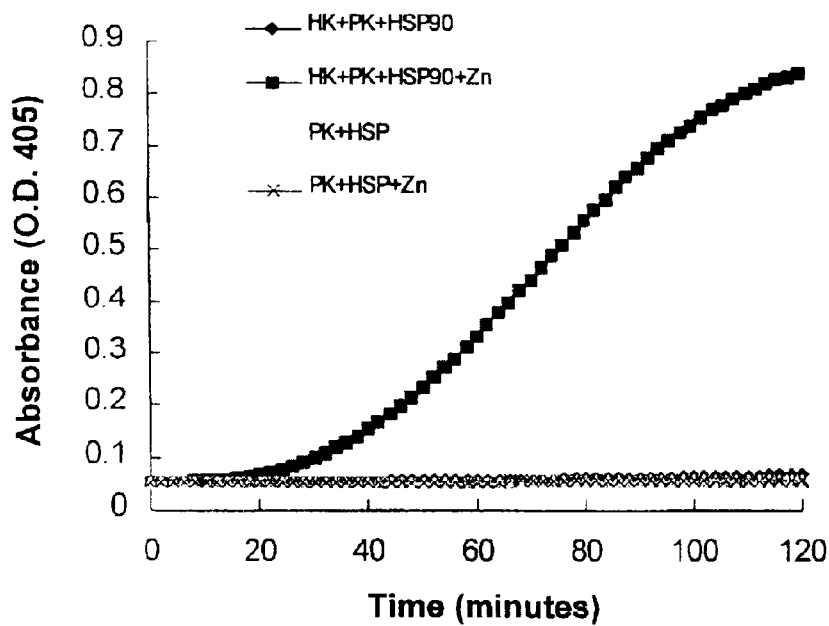
Figure 2  Prekallikrein activation on HSP90

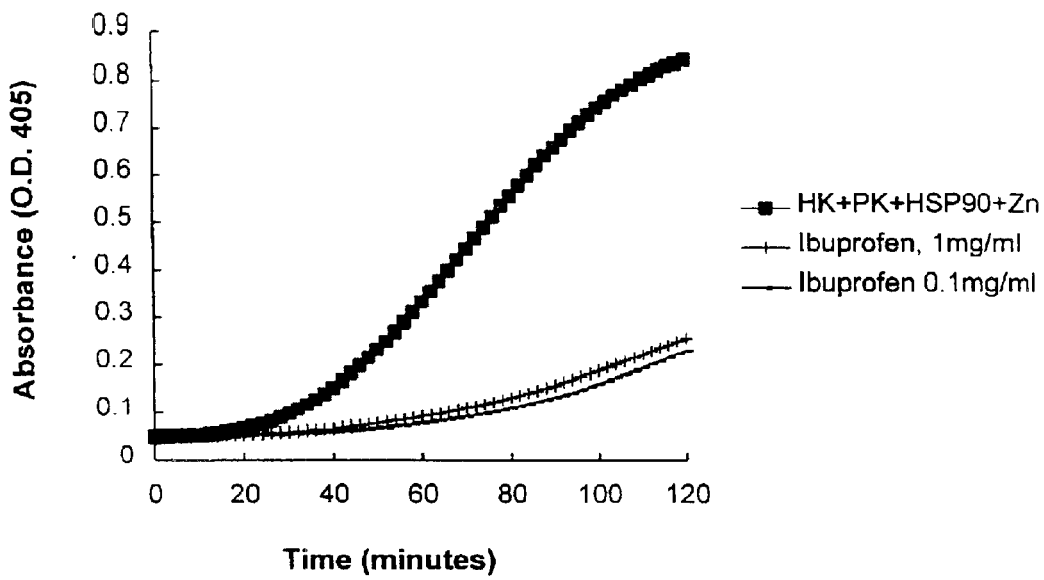
Figure 3 Prekallikrein activation on HSP90 and it's inhibition by Ibuprofen.
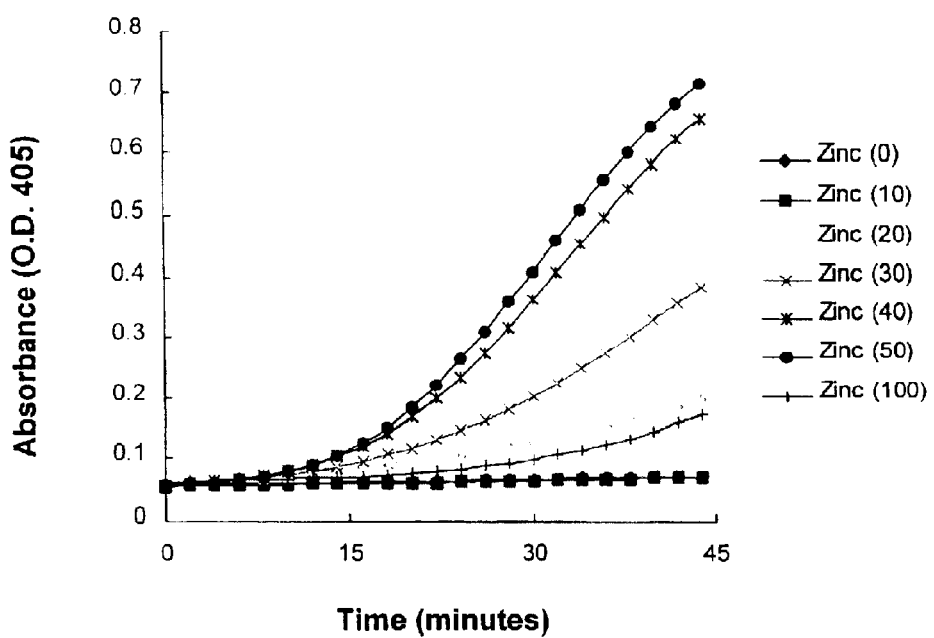
Figure 4 Effect of Zinc (μM) on PK activation

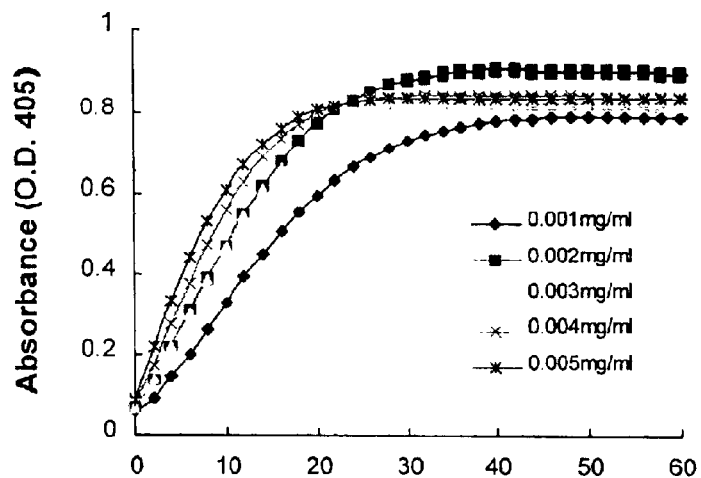
Figure 5    PK activation using 5μg/ml HK and varying concentration of PK. (for HSP90, Crude extract)
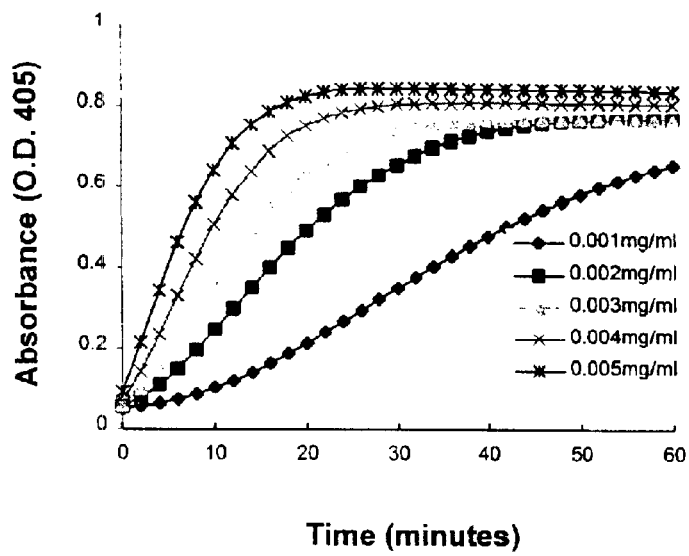
Figure 6    PK activation using 5μg/ml PK and varying concentration of HK. (for HSP90, Crude extract)

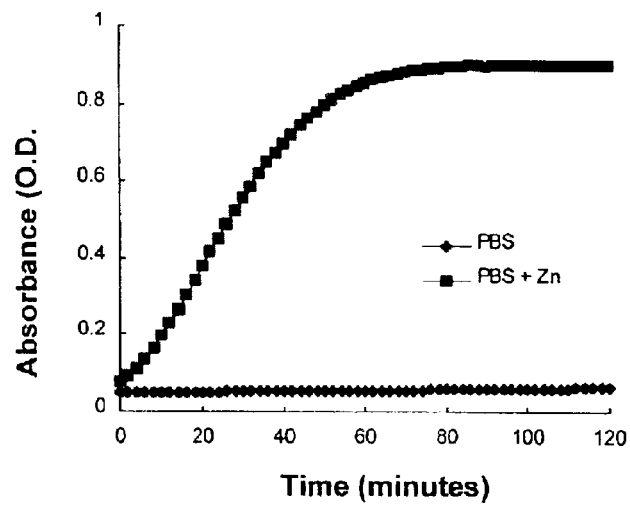
Figure 7    Prekallikrein activation with phosphate.
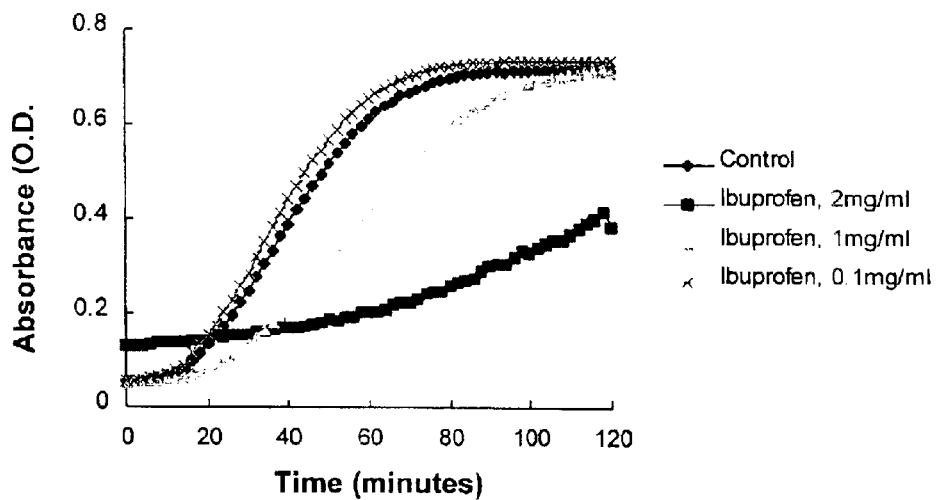
Figure 8    Prekallikrein activation with phosphate and inhibition by Ibuprofen.

PLASMA PREKALLIKREIN ACTIVATION AND KALLIKREIN PRODUCTION ASSAY

This application claims the benefit under 35 U.S.C. 119(e) of provisional application U.S. Ser. No. 60/315,800, filed Aug. 29, 2001 in the names of Allen P. Kaplan and Kusumam Joseph, for "Plasma Prekallikrein Activation and Kallikrein Production Assay," the disclosure of which is herein incorporated by reference in its entirety.

FIELD OF THE INVENTION

The present invention relates to a method for the activation of plasma prekallikrein using heat shock protein 90 (hereinafter abbreviated as HSP 90) or a phosphate ion in the absence of an activated blood coagulation factor XII (hereinafter abbreviated as FXIIa). Further, the present invention relates to a method for measuring an activity of a tested substance towards the production of plasma kallikrein produced in the plasma kallikrein activating system in the absence of FXIIa. More particularly, it relates to a method of measuring plasma kallikrein produced in said activating system.

BACKGROUND OF THE INVENTION

Kallikrein is a group of proteases widely distributed in the plasma and tissues of animals, and is known to participate in an enzyme reaction system called the plasma kallikrein-kinin system. An enzymatic system known as the plasma kallikrein-kinin system acts in vivo. It has a close relationship with various other enzymatic reaction systems such as the renin-angiotensin system, the blood clotting system, the fibrinolysis system, the complement system as well as the catecholamine and arachidonic acid cascades, which are mainly related to prostaglandins, leukotrienes and thromboxanes. Accordingly, the kallikrein-kinin system is closely associated with blood pressure regulating action and blood clotting-fibrinolysis-complement system action. Bioregulation and an improving action for peripheral circulation by various physiologically active substances produced by an arachidonic acid cascade are also related to the plasma kallikrein-kinin system. The plasma kallikrein-kinin system plays an important role in the regulation of functions in vivo.

Kinins, such as bradykinin, are produced in the plasma kallikrein-kinin system. They exhibit various physiological actions such as a decrease in blood pressure due to dilation of peripheral blood vessels, promotion of permeability of blood vessels, contraction or relaxation of smooth muscle, induction of pain, induction of inflammation, migration of leucocytes, liberation of catecholamine from the adrenal cortex, etc. Kinins are also known as mediators in acute inflammations, including allergic reactions, whereby their existence in vivo has a profound significance.

The plasma kallikrein-kinin system involves a series of enzyme reactions. Within the plasma kallikrein-kinin system, it is believed that a blood coagulation factor XII (a Hageman factor, hereinafter abbreviated as FXII) is activated in vivo by injury and invasive stimulation to tissues whereby a series of enzymatic reaction systems results. Thus, the activated blood coagulation factor XII (FXIIa) acts on the plasma prekallikrein (hereinafter abbreviated as PK) which exists in the same plasma to convert it to a plasma kallikrein which is an enzyme in an activated form. Then the plasma kallikrein acts on a high-molecular-weight kininogen (hereinafter abbreviated as HK) to liberate bradykinin, which is a nonapeptide.

Kinins such as bradykinin, which are liberated by the enzymatic reaction of the plasma kallikrein-kinin system, exhibit various physiological actions as mentioned already. Accordingly, substances which inhibit the action of bradykinin or substances which inhibit the production of bradykinin by interfering with the formation of kallikrein maybe useful as anti-inflammatory, analgesic and antiallergic agents.

Therefore, establishment of a method for measuring the degree to which substances, compounds or components inhibit or promote the production of kallikrein in a reliable, simple, easy, quick and precise manner is a very important means for ascertaining the action which helps the above-mentioned bioregulation systems. It is also useful for developing drugs for regulating or controlling the bioregulation systems.

When screening or evaluating drugs using plasma prekallikrein-activation are carried out in vitro, activation of prekallikrein through activation of FXII by an invasive stimulation to tissues and injury such as an intravital reaction cannot be conducted. A substance which activates the prekallikrein may be added to an isolated plasma to carry out a reaction which induces plasma kallikrein production in vitro.

However, the plasma of animals contain various components in addition to the above-mentioned components. For example, components which have an effect (such as an inhibition or a promotion) on plasma kallikrein production and other unknown factors are contained in animal plasma. Accordingly, when the activity of the tested substance towards the production of kallikrein is measured utilizing the above-mentioned reaction system with an objective of screening or the like of drugs using the plasma prekallikrein activation system, use of animal plasma per se is complicated by various factors containing unknown components which may affect the plasma kallikrein-kinin reaction system. Consequently, controlling the reaction system is highly technical and complex when animal plasma is used as a source of reactants.

Specific examples of the method for measuring the activity of drugs for suppressing pain, inflammation, allergy, etc. induced by bradykinin, such as an analgesic agent, an anti-inflammatory agent, an antiallergic agent, etc. the above-mentioned drugs are: (1) a method of measuring the inhibiting activity of a test substance to monitor the production of kallikrein using animal plasma, U.S. Pat. No. 4,985,354; (2) a method of measuring the inhibiting and promoting activities of a test substance to the production of FXIIa using animal plasma, U.S. Pat. No. 5,599,683; and (3) a method of measuring the inhibiting and promoting activity of a test substance to the production of FXIIa, kallikrein or bradykinin by a reconstituted plasma kallikrein-kinin system, U.S. Pat. No. 5,648,228. However, as discussed above, test materials containing plasma are impure and interfere with or inhibit kallikrein production.

In U.S. Pat. No. 5,648,228, the reconstituted plasma kallikrein-kinin reaction system for measuring the physiological action of a tested substance combines FXII, PK, and preferably HK, each being substantially purified. However, to produce kallikrein in this system, a heterologous surface having a negative charge (kaolin) is further required to activate FXII and, thus, to activate PK. It would be desirable to produce a prekallikrein-activating substance, produced in living organisms, in a pure or isolated form, in which interfering or competing components (e.g. protease inhibitors) or other factors are substantially or completely absent, for a more faithful reproduction of an actual prekallikrein-activating reaction in living organisms.

Until now, it has been believed that prekallikrein is activated to kallikrein by FXIIa. Thus, all of the above-mentioned methods are based on the prekallikrein-activating system by activation with FXIIa. On the contrary, the present inventors have found a novel prekallikrein-activating system in which FXIIa does not participate. Use of this prekallikrein-activating system makes it possible to carry out the screening of an inhibitor on the production of kallikrein based on a new biological mechanism. In addition, since we can obtain new knowledge or information about the kallikrein-producing system, the prekallikrein-activating method of the present invention is very useful.

SUMMARY OF THE INVENTION

The present invention provides an activator for prekallikrein which is selected from the group consisting of heat shock protein 90 (HSP 90), a phosphate ion and mixtures thereof. The present invention also comprises a method for activating prekallikrein to produce kallikrein by use of said prekallikrein activator in the absence of FXIIa, a known prekallikrein activator. The method is useful in measuring in vitro the activity of a test substance with respect to inhibiting or promoting the production of kallikrein. The tested substance's ability to inhibit or promote the production of kallikrein in the absence of FXIIa can be measured in a simple, reliable, convenient, prompt and precise manner by the method of the present invention.

The prekallikrein activator of the present invention comprises part of an in vitro system for activating prekallikrein to produce kallikrein by use of said activator in the absence of FXIIa. An in vitro system of the present invention comprises an activator composition of HSP 90, a phosphate ion and mixtures thereof, as well as HK and zinc ion.

The method of the present invention for activating prekallikrein comprises mixing prekallikrein with the prekallikrein activator of phosphate and/or HSP 90, a composition comprising HK and zinc ions. A method for evaluating the activity of a test drug for the production of kallikrein comprises activating prekallikrein by mixing prekallikrein with HSP 90 or phosphate, HK and zinc ions in the presence of said drug, and determining degree of production of kallikrein. The test drug may be selected from the group consisting of analgesic, anti-allergy and anti-inflammatory drugs, for example, the inhibiting activities of ibuprofen, ketoprofen and the like may be measured. The amount of physiologically active substance produced relative to the amount produced in a control sample which does not contain the tested substance or which contains a different test substance may be used to indicate the relative activity of the tested substance.

Conducting the plasma prekallikrein activating reaction in the system of the present invention avoids complications associated with the use of plasma per se as a source of the physiologically active substances, such as plasma prekallikrein. The HSP 90 activator is isolated and purified from the cytosolic extract of a human endothelial cell. The HK and PK components of the system of the present invention may be separated or purified from plasma or manufactured using genetic engineering techniques. The system of the present invention can be made using off the shelf water soluble sources of zinc and phosphate ion.

BRIEF DESCRIPTION OF THE DRAWINGS

FIG. 1 is a graph showing the changes in the absorbance as a function of incubation time in the measuring method of the present invention wherein the absorbance corresponds to the amount of plasma kallikrein produced in the presence of prekallikrein and purified, isolated Human Umbilical Vein Endothelial Cells (hereinafter abbreviated as HUVEC) cells, in the presence of prekallikrein, HK, and purified, isolated HUVEC cells, in the presence of prekallikrein, zinc, and purified, isolated HUVEC cells, and in the presence of prekallikrein, HK, zinc and purified, isolated HUVEC cells.

FIG. 2 is a graph showing the changes in the absorbance as a function of incubation time in the measuring method of the present invention wherein the absorbance corresponds to the amount of plasma kallikrein produced in the presence of prekallikrein, HK and HSP 90, in the presence of prekallikrein, HK, HSP 90 and zinc, in the presence of prekallikrein and HSP 90, and in the presence of prekallikrein, HSP 90 and zinc.

FIG. 3 is a graph showing the results in the measurement of the inhibiting activity of ibuprofen towards the production of plasma kallikrein using an HSP 90 activator in the activity measuring method of the present invention.

FIG. 4 is a graph showing the effect of zinc concentration ($\mu$M) on plasma prekallikrein activation in the presence of HK and HSP 90.

FIG. 5 is a graph showing the effect of varying plasma kallikrein concentration on the activation of plasma prekallikrein in the presence of 5 $\mu$g/ml HK and HSP 90.

FIG. 6 is a graph showing the effect of varying HK concentration on the activation of plasma prekallikrein in the presence of 5 $\mu$g/ml plasma kallikrein and HSP 90.

FIG. 7 is a graph showing the changes in the absorbance as a function of incubation time in the measuring method of the present invention wherein the absorbance corresponds to the amount of plasma kallikrein produced in the presence of prekallikrein, HK and phosphate buffered saline (hereinafter abbreviated as PBS) and in the presence of prekallikrein, HK, PBS and zinc.

FIG. 8 is a graph showing the results in the measurement of the inhibiting activity of ibuprofen towards the production of plasma kallikrein using a phosphate ion activator in the activity measuring method of the present invention.

DETAILED DESCRIPTION OF THE INVENTION

The present invention provides an activator for prekallikrein which is selected from the group consisting of heat shock protein 90 (HSP 90), a phosphate ion and mixtures thereof. The present invention also comprises a method for activating prekallikrein to produce kallikrein by use of said prekallikrein activator in the absence of FXIIa, the method being useful in measuring in vitro the activity of a test substance with respect to inhibiting or promoting the production of kallikrein. The tested substance's ability to inhibit or promote the production of kallikrein, is measured in a simple, reliable, convenient, prompt and precise manner by the method of the present invention.

The prekallikrein activator of the present invention comprises part of an in vitro system for activating prekallikrein to produce kallikrein in the presence of said activator. An in vitro system of the present invention comprises an activator composition of HSP 90, a phosphate ion and mixtures thereof, as well as HK and zinc ion.

In the present invention, a substance is tested or measured for its ability to inhibit or promote the production of plasma kallikrein. The test may be conducted in vitro by starting the activation of plasma prekallikrein in the presence of the test substance in a plasma prekallikrein activating system. The measuring method may be conducted, for example, by admixing plasma prekallikrein, HK, zinc ion and an activator selected from the group consisting of HSP 90, phosphate ion and mixtures thereof to initiate activation of plasma prekallikrein in the presence of the test substance. The quantitative amount of physiologically active substance such as kallikrein or bradykinin produced in the reaction is an indication of the effectiveness or activity of the tested substance in promoting or inhibiting the production of the physiologically active substance in a physiological reaction system involving plasma prekallikrein. The effect of the tested substances on production of plasma kallikrein, and, indirectly, bradykinin may be used to screen them for usefulness as anti-inflammatory, analgesic, and antiallergic drugs.

With respect to the constituting components in the plasma prekallikrein activating system in the measuring method of the present invention, plasma prekallikrein can be used when the physiologically active substance to be determined is plasma kallikrein. A preferred reaction system may also be constructed by adding HK thereto. With regard to each of those constituting components, that which is substantially purified may be used. The plasma prekallikrein, and HK which are utilized in producing the reconstituted plasma prekallikrein activation systems may each be separated or purified from plasma or manufactured by a means of gene technology. The plasma of any animal may be used as the source of the purified or separated components provided it has a blood clotting system and a plasma kallikrein-kinin system. For example, human plasma and plasma of animals such as bovines, sheep, pigs, horses, goats, monkeys, dogs, cats, rabbits, guinea pigs, hamsters, rats or mice may be utilized as sources of the components. Preferably, human plasma is used as the source of the components used in obtaining the reconstituted plasma kallikrein-kinin reaction systems.

Zinc ion may be obtained from any pharmaceutically acceptable salt or water-soluble source, such as zinc chloride, zinc phosphate, zinc acetate, etc., and mixtures thereof.

The activating agent for plasma prekallikrein comprises an activator selected from the group consisting of HSP 90, phosphate ion, and mixtures thereof. HSP 90, a cell-free protein, may be isolated and purified from a cytosolic extract of human endothelial cells using known methods. The source of the phosphate ion may comprise any known pharmaceutically acceptable salt or water soluble form of phosphate ion, such PBS, zinc phosphate, calcium phosphate, sodium phosphate etc., and mixtures thereof. Each of the plasma prekallikrein activators of the present invention can activate plasma prekallikrein in the absence of FXIIa. The plasma prekallikrein activators of the present invention can be used either solely or jointly and may be selected in effective concentrations for activating plasma prekallikrein.

As examples of test substances evaluated by the measurement of activity for inhibiting plasma kallikrein production in accordance with the present invention ibuprofen, indomethacin, ketoprofen, aminopyrine, ketotifen, ketoprofen, pentazocine and DSCG can be tested. These drugs are used as analgesic, anti-inflammatory or antiallergic drugs in accordance with the method of measuring the kallikrein production inhibition activity according to the present invention.

An example of useful concentrations of components in the in vitro system of the present invention comprise:

About 0.001 mg/ml to about 0.005 mg/ml, preferably about 0.002 mg/ml to about 0.003 mg/ml, of plasma prekallikrein;

About 0.001 mg/ml to about 0.005 mg/ml, preferably about 0.003 mg/ml to about 0.005 mg/ml, of HK;

About 0.001 mg/ml to about 0.01 mg/ml, preferably about 0.003 mg/ml to about 0.007 mg/ml, of HSP 90 and/or about 0.3 mM to about 5 mM, preferably about 0.5 mM to about 1 mM, of phosphate ion;

About 10 $\mu$M to about 100 $\mu$M, preferably about 30 $\mu$M to about 50 $\mu$M, of zinc ion;

About 0.1 mg/ml to about 5 mg/ml, preferably about 0.1 mg/ml to about 1 mg/ml, of a test drug substance; and, About 0.1 mM to about 1 mM, preferably about 0.3 mM to about 0.6 mM, of a kallikrein substrate for use in quantitatively determining kallikrein.

In the mixing reaction carried out by adding a prekallikrein activator to a solution comprising a substantially purified plasma prekallikrein and preferably HK, the reaction temperature may be suitably adjusted so as to make the reaction easily controllable. For example, the reaction may be carried out at temperatures ranging from about room temperature to a reaction temperature of 0° C. to 4° C. using an ice water bath. It is preferred that the mixing reaction is carried out at a pH where the plasma kallikrein-kinin system reaction smoothly proceeds, such as from 7.0 to 9.0. In order to adjust to a suitable reaction condition, salts such as sodium chloride, metal ions such as zinc ion and other additives and auxiliary agents which are commonly used in this art may be added to the reaction system.

The reaction time for the mixing reaction maybe adjusted depending upon the concentrations of the above-mentioned plasma prekallikrein activators, plasma prekallikrein, HK, zinc and the tested substance, as well as upon the pH of the reaction solution. However, when the produced amount of the kallikrein to be quantitatively determined is saturated, it is not possible to correctly evaluate the action of the tested substance. Therefore, it is preferred to set the reaction time so that it is less than the time it takes for production of a saturated amount of the kallikrein to be determined.

In embodiments of the invention the reaction time may be fixed or "set." The reaction time can be "set" by stopping the production of kallikrein, for example, by adding a prekallikrein activation inhibitor to the system of the present invention after a desired reaction time. Also, by adding a coloring or fluorescent synthetic substrate to the reaction system from the start or beginning, the produced amount of kallikrein (coloring or fluorescent intensity) may be observed at different lapses of time. Various inhibitors were tested and are shown along with their typical concentrations in the system of the present invention, in Table 1. When the reaction is stopped, the produced kallikrein can be quantitatively determined using an enzymatic activity of kallikrein as a target, for example, by applying a substrate to kallikrein.

TABLE 1

Inhibition Profile of PK Activation.

| Inhibitors | Concentration | % inhibition |
|---|---|---|
| Antipain | 100 $\mu$M | 98.6 |
| Aprotinin | 100 $\mu$M | 96.4 |
| Captopril | 10 mM | 97.9 |
| Corn Trypsin Inhibitor | 10 $\mu$M | 94.3 |
| Cystatin | 10 $\mu$g/ml | 4.5 |

TABLE 1-continued

Inhibition Profile of PK Activation.

| Inhibitors | Concentration | % inhibition |
|---|---|---|
| Cysteine | 10 mM | 59.6 |
| DTT | 10 mM | 69.1 |
| EDTA | 20 mM | 85.4 |
| Glutathione | 100 µM | 18.6 |
| $HgCl_2$ | 1 mM | 98 |
| Iodoacetamide | 10 mM | 7 |
| LBTI | 50 µg/ml | 0 |
| Mercaptoethanol | 5% | 85.5 |
| PMSF | 2 mM | 5 |
| SBTI | 50 µg/ml | 98.6 |

In the correct quantitative determination of a plasma kallikrein, it is preferred to use inhibitors which stop the production of plasma kallikrein. Inhibitors such as antipain, aprotinin, captopril, corn trysin inhibitor (CTI), cystatin, cysteine, DTT, EDTA, glutathione, $HgCl_2$, iodoacetamide, lima bean trypsin inhibitor (LBTI), mercaptoethanol, PMSF and soybean trypsin inhibitor (SBTI) were tested in this system in order to find out a preferred inhibitor of the prekallikrein activating factor (Table 1). Among them, antipain, aprotinin, captopril, CTI, EDTA, $HgCl_2$, mercaptoethanol and SBTI were good inhibitors of the activator in this system. When the reaction is stopped, the produced plasma kallikrein can be determined using an enzymatic activity of the plasma kallikrein as a target by utilizing a substrate to the plasma kallikrein.

The concentration of the substances which are used for stopping the production of kallikrein may be suitably selected so that the quantitative determination of each of kallikrein is not substantially affected.

Quantitative determination of the produced physiologically active substance may be carried out by conventional measuring methods. In the quantitative determination of the produced plasma kallikrein, known methods in which a natural substrate such as HK, a coloring synthetic substrate such as H-D-Pro-Phe-Arg-pNA (S-2302) or Bz-Pro-Phe-Arg-pNA or a fluorescent synthetic substrate such as Z-Phe-Arg-MCA may be used as well. Various methods for the quantitative determination of the produced plasma kallikrein are disclosed in U.S. Pat. No. 4,985,354 and U.S. Pat. No. 6,117,648. The disclosures of U.S. Pat. No. 4,985,354 and U.S. Pat. No. 6,117,648 are herein incorporated by reference in their entireties.

Besides the above-mentioned measuring methods using the substrates, immunological measuring methods such as a radioimmunoassay (RIA) or an enzyme immunoassay (EIA), quantitative determination using chromatography, etc., may be used too.

Any method may be chosen depending upon the conditions such as the number of the tested substances, devices in the measuring facilities, preciseness requested for the measurement, etc. In addition, the degree of the prekallikrein activation can be measured by determination of bradykinin production. Bradykinin production may be determined by known or conventional methods.

The present invention is further illustrated by way of the following non-limiting examples and materials and methods used therein, wherein all parts, percentages and ratios are by weight and all temperatures are in degrees C., unless otherwise indicated:

Materials and Methods

A. Endothelial Cell Culture Used in Isolating and Purifying HSP 90.

Human Umbilical Vein Endothelial Cells (HUVEC) were isolated according to Jaffe and cultured in gelatin coated dishes in endothelial growth medium (EGM Bullet kit, Clonetics, San Diego, Calif.). See Jaffe EA., *Ann N Y Acad Sci* 1982; 401: 163–170. For prekallikrein activation assays the cells were subcultured into gelatin-coated 96-well plates in 0.2 ml culture medium. The cells were identified as endothelial cells by their distinct cobblestone morphology and interaction with antiserum to Von Willebrand Factor. All cells were used at the third cell passage.

B. Cell Isolation and Preparation of Cytosolic (S100) Extracts from Endothelial Cell Culture.

Confluent HUVEC monolayers from the culture produced in A, above, were washed three times with cold Hepes buffered saline (HBS, pH 7.4) and the cells were gently scraped into HBS on ice using a Teflon spatula. The cells were collected gently by low-speed (1,000×g) centrifugation, resuspended in HBS transferred to a polypropylene ultracentrifuge tube, and collected again by centrifugation. The HBS was aspirated completely from the cell pellet. The cells were then subjected to ultracentrifugation (100,000×g) for 90 minutes at 4° C. The resulting supernatant fraction was transferred to Eppendorf tubes and stored at 0° C.

C. Preparation of an Affinity Column for Isolating Labeling Proteins.

Purified corn trypsin inhibitor (CTI, Enzyme Research Laboratories, South Bend, Ind.) was coupled to an Ultralink Biosupport medium (Pierce) according to the manufacturer recommendations.

D. Biotinylation (Labeling) of Proteins.

Biotinylation of CTI was performed using NHS-LC-biotin according to the following procedure. CTI (1 mg in 500 µl) were first dialyzed against 0.2 M $NaHCO_3$ buffer (pH 8.3). Labeling was initiated by addition of 50 µl of 1 mg/ml solution of biotin freshly dissolved in dimethyl sulfoxide. The reaction was allowed to proceed for four hours at room temperature with constant but gentle mixing. After the incubation the protein was dialyzed against PBS. Biotinylation was verified by ELISA using wells coated with various dilutions of the labeled protein and probing with alkaline phosphatase conjugated Avidin or Streptavidin.

E. Purification of CTI Binding Proteins Used as Probes to Identify the Prekallikrein Activating Factor from a Cytosolic Extract.

The CTI affinity column was equilibrated with HBS containing 50 µM zinc chloride. The S100 fraction was loaded on the column and incubated for one hour with end-over-end mixing. After incubation the flow through was collected and saved for later analysis. The column was washed with 10 volumes of HBS followed by 10 volumes of 0.25 M NaCl. The washings were also collected and saved. The bound proteins were eluted with 0.5 M NaCl and 0.5 ml fractions were collected. The fractions from all the steps were assayed for activity of the prekallikrein activating factor.

F. Electrophoresis and Ligand Blot Analysis.

Samples were prepared in Laemmli buffer and loaded on to 10% SDS-polyacrylamide gel (5% stack) and subjected to gel electrophoresis. See Laemmli UK., *Nature*, 1970; 227: 680–685. After electrophoresis, the gels were either stained or transferred to nitrocellulose membranes and were probed with biotinylated ligand. Bound probes were visualized by alkaline phosphatase-conjugated Avidin.

G. Protein Determination (for Corroborating the Concentration of any Protein Used in Accordance with the Present Invention).

Protein concentrations were determined by the method of Bradford using human IgG as reference protein. See Bradford M M., *Anal Biochem* 1976; 72: 248–254.

EXAMPLE 1

Prekallikrein Activation Assays

Assays were performed in HEPES buffered saline (HBS) (10 mM Hepes, 137 mM NaCl, 4 mM KCl, 11 mM D-glucose, and 0.5 mg/ml RIA grade bovine serum albumin, pH 7.4), with a kallikrein specific substrate (0.6 mM S-2302). For assays using the cell-free system, 96 well disposable polystyrene microtiter plates (Dynatech Laboratories, Chantilly, Va.) were used. These microtiter plates were pretreated with 1% polyethylene glycol (Aquacide III, Calbiochem, Calif.) in HBS for two hours to prevent adsorption of proteins to polystyrene. The absorbance (O.D. at 405 nm or optical density at 405 nm) was monitored at room temperature on a Molecular Devices (Sunnyvale, Calif.) THERMOmax microplate reader. Just prior to the assay all the proteins were treated with 2.0 mM (4-amidinophenyl)methanesulfonyl fluoride (APMSF) for 15 minutes at pH 5.5, after which they were diluted 1:100 with HBS and incubated for 45 minutes to allow for the decomposition of any unreacted APMSF at the neutral pH. The proteins were treated with APMSF before use and were inactivated for the sake of safety.

Results of Prekallikrein Activation Assays

Studies were performed to determine whether prekallikrein could be activated on the surface of HUVEC. There was no kallikrein activity when HK or prekallikrein was added alone with HUVEC. However, when HUVEC were incubated with HK and prekallikrein together in the presence of zinc, chromogenic activity was detected (FIG. 1). There was no activation if either HK or zinc is omitted. Addition of Factor XII along with HK and prekallikrein augmented the activation. Since the activation in the absence of Factor XII that was observed on HUVEC did not happen on an inorganic, negatively charged surface such as dextran sulfate, we considered the possibility that a prekallikrein activating factor is either present on the surface of HUVEC or secreted by the cells. In order to determine whether the prekallikrein activator was membrane bound or intracellular, the activation assay was performed in a cell-free system using a cytosolic extract and membrane fraction as activator. Both, cytosolic extract and the membrane fraction activated the system to the same extent. The activation was observed only in the presence of both HK and zinc in each instance. Thus it was decided to purify and identify the activating factor from the cytosolic extract.

Effect and Optimum Concentration of Zinc.

The effect and the optimum concentration of zinc was determined with the cell-free system. Using the cytosolic extract as the activator and HBS-BSA buffer, the optimum concentration of zinc was found to be 50 $\mu$M (FIG. 4). In the absence of zinc, there was no detectable activity. For all the experiments using zinc, a concentration of 50 $\mu$M was used.

Effect of HK in the Activation of Prekallikrein.

Incubated together were prekallikrein, cytosolic extract, and zinc in the presence and in the absence of HK. The results showed that in the absence of HK, there was no prekallikrein activation. As well as zinc, the optimum concentrations of HK and prekallikrein were determined (FIGS. 5 and 6).

EXAMPLE 2

Purification of the Prekallikrein Activating Factor

Since prekallikrein activation in this system could be inhibited by CTI, CTI was used as an affinity ligand to purify the proteins that bind to CTI. The activity of the prekallikrein activator was retained on the affinity column when CTI was used as affinity ligand. The CTI bound enzymatic activity was eluted with 0.5 M NaCl in HBS. The eluted fractions were dialyzed to remove the high salt content and assayed to confirm the activity. The proteins from the active fractions were separated by SDS-PAGE and transferred to nitrocellulose membrane for a ligand blot with biotinylated CTI. Ligand blot analysis revealed that biotinylated CTI bound to two major bands at about 60 and 90 kDa. Although a Coomassie Blue stain of the gel showed several protein bands, they were well separated and it was possible to get an amino acid sequence of these proteins.

Amino Acid Sequence Analysis and Identification of the Isolated Proteins.

Proteins separated by SDS-PAGE were transferred to immobilon$^{PSQ}$ membranes and stained with Coomassie Blue stain. Individual bands corresponding to those blotted with biotinylated CTI were cut out and sequenced after digestion in order to get an internal peptide. Sequence analysis was done by Midwest Analytical Inc.(St. Louis, Mo.). The sequence of 12 amino acids obtained from the analysis matched 100% with the residues 2–13 of heat shock protein 90.

Western Blot of the Isolated Protein Using Antibody to HSP 90

Proteins from the cytosolic extract and the active fractions eluted from the CTI affinity column were separated by SDS-PAGE and were transferred for Western blot assay using an antibody to HSP 90.

EXAMPLE 3

Prekallikrein Activation Using Purified HSP 90

HSP 90 was confirmed as a prekallikrein activator, which was functionally indistinguishable from the cytosolic extract (FIG. 2). A HUVEC activator system was functionally effective as well (FIG. 1). Activation was HK- and zinc-dependent and was inhibited by CTI. The incubation mixture used is as follows:

HSP 90 activator system.

50 $\mu$L buffer (HBS-BSA)
10 $\mu$l HSP90 (50 $\mu$g/ml)
10 $\mu$l Zinc chloride (500 $\mu$M)
10 $\mu$l HK (35 $\mu$g/ml)
10 $\mu$l PK (25 $\mu$g/ml)
10 $\mu$l S-2302 (6 mM)
HUVEC activator system (in addition to the isolated HUVEC culture used therein).
60 $\mu$l buffer (HBS-BSA)
10 $\mu$l Zinc chloride (500 $\mu$M)

10 μl HK (35 μg/ml)

10 μl PK (25 μg/ml)

10 μl S-2302 (6 mM)

Incubate at room temperature, measuring O.D. at 405 nm every 2 minutes

HBS: HEPES buffer, BSA: Bovine serum albumin,

HK: High molecular weight kininogen, PK: Prekallikrein,

S-2302: H-D-Pro-Phe-Arg-p-nitroanilide (kallikrein specific substrate)

EXAMPLE 4

Inhibition of HSP 90-Dependent Prekallikrein Activation by Ibuprofen.

HSP 90-dependent prekallikrein activation was inhibited by Ibuprofen dose-dependently (FIG. 3). Therefore, the new prekallikrein activating system is useful for a screening to evaluate a test drug for the production of kallikrein.

EXAMPLE 5

Prekallikrein Activation by Phosphate Ion

The inventors found that prekallikrein was activated to kallikrein in the absence of any activator such as FXIIa, HUVEC or HSP 90 (FIG. 7). The activation of prekallikrein in the presence of phosphate and zinc ions was inhibited by Ibuprofen dose-dependently (FIG. 8).

Incubation Mixture

50 μl buffer (HBS-BSA)

10 μl PBS (10 mM)

10 μl Zinc chloride (500 μM)

10μl HK (35 μg/ml)

10 μl PK (25 μg/ml)

10 μl S-2302 (6 mM)

Incubate at room temperature, measuring O.D. at 405 nm. every 2 minutes.

HBS: HEPES buffer, BSA: Bovine serum albumin,

PBS: Phosphate buffered saline, HK: High molecular weight kininogen,

PK: Prekallikrein,

S-2302: H-D-Pro-Phe-Arg-p-nitroanilide (kallikrein specific substrate)

Until now, it has been believed that prekallikrein is activated to kallikrein by FXIIa. On the contrary, the present invention provides a new plasma prekallikrein-activating system in the absence of FXIIa. The usefulness of the present invention is:

1. The new prekallikrein-activating system is helpful for an investigation to clarify the activating mechanism of plasma prekallikrein.

2. The new system of the present invention is useful to elucidate the meaning of a prekallikrein-activating system in the absence of FXIIa, a known activator of prekallikrein.

3. It is also useful to carry out a screening of new analgesic, anti-inflammatory or anti-allergic drugs based on a different pharmacological mechanism from the known prekallikrein-activating system in which FXIIa participates.

The method of measuring the activity according to the present invention utilizing the plasma prekallikrein activating system provides a reaction system in which the contaminating other factors are substantially removed. Therefore, it is not necessary to regulate the reaction to compensate for the factors which may affect the enzymatic reaction system of the plasma kallikrein-kinin system and unknown components therein. Accordingly, the activity (a promoting or inhibiting ability) of the tested substance towards the production of plasma kallikrein in the absence of FXIIa can be measured in an easy, convenient prompt and precise manner.

In the measuring method of the present invention, each off-the-shelf component (e.g. phosphate) or substantially purified component is used in place of the animal plasma. The advantages of using the substantially purified components to form a plasma prekallikrein activation system compared to using a conventional animal plasma are:

1. The amount of each of the constituting components can be freely adjusted and, accordingly, reaction time, reaction temperature, absorbance, etc. in the reaction system can be suitably chosen depending upon the numbers of the tested substances and the required precision.

2. The influence of the endogenous inhibitors such as protease inhibitors, $\alpha_2$ macroglobulin and C1-inhibitor, and kininase being present in the animal plasma can be substantially neglected. In addition, it is not necessary to take the factors which may affect the reaction and unknown substances in the animal plasma into consideration.

3. The scattering in the reactions due to the lack of uniformity in the components of animal plasma can be prevented whereby an increase in the precision of the measurement results.

4. Because FXIIa is not used to activate plasma prekallikrein, substantial cost savings and process economies result. Where phosphate ion is used as the prekallikrein activator, the ordinary skilled artisan can procure all necessary reagents except HK without any of the expensive protein isolation and purification steps.

In the quantitative determination of the produced physiologically active substances in the measuring method of the present invention, various methods of measuring the inhibiting ability against the production of plasma kallikrein can be suitably selected. Accordingly, the degree of freedom in the measurement and the applicable range are broad.

Furthermore, in the method for measuring the activity of the present invention, an activation system wherein each component is substantially purified is used and the contaminating other factors are removed makes it possible to screen drugs or compounds having activity towards the production (a promoting or an inhibiting activity for the production) of plasma kallikrein from several viewpoints. The screening of drugs or compounds may be based upon a clear and specific action mechanism. Accordingly, the present invention achieves a significant beneficial effect on the development of new drugs for various diseases.

What is claimed is:

1. A method for evaluating the activity of a test drug towards the production of kallikrein comprising activating prekallikrein by mixing prekallikrein with high molecular weight kininogen, zinc ions and isolated or purified heat-shock protein 90 with said drug, and determining the degree of production of kallikrein.

2. The method for evaluating the activity of a test drug towards the production of kallikrein of claim 1, wherein the test drug is selected from the group consisting of analgesic, anti-allergy and anti-inflammatory drugs.

3. The method for evaluating the activity of a test drug towards the production of kallikrein of claim 1, wherein the produced plasma kallikrein is quantitatively determined by using a substrate to the plasma kallikrein.

4. The method for evaluating the activity of a test drug towards the production of kallikrein of claim 3, wherein said substrate to the plasma kallikrein is selected from the group consisting of a natural substrate, a coloring synthetic substrate and a fluorescent synthetic substrate.

5. The method for evaluating the activity of a test drug of claim 1 wherein the degree of the prekallikrein activation is measured by determination of bradykinin production.

6. The method for evaluating the activity of a test drug of claim 1 wherein the prekallikrein is activated to produce kallikrein in the absence of FXIIa.

7. The method for evaluating the activity of a test drug of claim 1, wherein the heat-shock protein 90 is purified.

8. A method for activating prekallikrein comprising mixing prekallikrein with high molecular weight kininogen, zinc ions and isolated or purified heat-shock protein 90 to form an activated mixture.

9. The method for activating prekallikrein of claim 8, wherein said mixture further comprises phosphate.

10. The method for activating prekallikrein of claim 8 wherein the prekallikrein is activated to produce kallikrein in the absence of FXIIa.

11. The method for activating prekallikrein of claim 8, wherein the heat-shock protein 90 is purified.

12. The method for activating prekallikrein of claim 8, wherein the prekallikrein is separated or purified.

13. The method for activating prekallikrein of claim 8, wherein the prekallikrein is purified.

14. The method for activating prekallikrein of claim 8, wherein the high molecular weight kininogen is separated or purified.

15. The method for activating prekallikrein of claim 8, wherein the high molecular weight kininogen is purified.

16. The method for activating prekallikrein of claim 8, wherein said mixing is carried out in vitro.

17. A composition for evaluating the activity of a test drug towards the production of kallikrein comprising prekallikrein, high molecular weight kininogen, zinc ions and isolated or purified heat-shock protein 90.

18. The composition of claim 17 further comprising phosphate ions.

19. The composition of claim 17, wherein the heat-shock protein 90 is purified.

20. The composition of claim 17, wherein the prekallikrein is separated or purified.

21. The composition of claim 17, wherein the prekallikrein is purified.

22. The composition of claim 17, wherein the high molecular weight kininogen is separated or purified.

23. The composition of claim 17, wherein the high molecular weight kininogen is purified.

* * * * *

UNITED STATES PATENT AND TRADEMARK OFFICE
CERTIFICATE OF CORRECTION

PATENT NO. : 6,913,900 B2
DATED : July 5, 2005
INVENTOR(S) : Allen P. Kaplan and Kusumam Joseph It is certified that error appears in the above-identified patent and that said Letters Patent is hereby corrected as shown below:

Title page
Item [74], *Attorney, Agent or Firm*, replace "Holland Law Firm, P.L.C." with
-- Hollander Law Firm, P.L.C. --.

Signed and Sealed this

Sixth Day of September, 2005

JON W. DUDAS
*Director of the United States Patent and Trademark Office*